United States Patent [19]

Brown et al.

[11] 4,048,186
[45] Sept. 13, 1977

[54] ANTIBACTERIAL SUBSTITUTED AZETIDINONES

[75] Inventors: Allan Guildford Brown, Cranleigh; Thomas Trefor Howarth, Rudgwick, both of England

[73] Assignee: Beecham Group Limited, England

[21] Appl. No.: 618,013

[22] Filed: Sept. 30, 1975

[30] Foreign Application Priority Data

Oct. 28, 1974 United Kingdom ............... 46626/74

[51] Int. Cl.$^2$ ............................................ C07D 263/18
[52] U.S. Cl. ............................... 260/307 FA; 424/272
[58] Field of Search ................................. 260/307 FA Primary Examiner—Donald G. Daus
Assistant Examiner—D. B. Springer
Attorney, Agent, or Firm—Jacobs & Jacobs

[57] ABSTRACT

Substituted azetidinones having antibacterial activity and pharmaceutically acceptable salts and esters thereof and pharmaceutical compositions containing an antibacterially effective amount of such an azetidinone. A representative compound is methyl 3-(2'-hydroxyethyl)-7-oxo-1-aza-4-oxabicyclo[3,2,0]-heptane-2-carboxylate. The daily dosage is between 50 and 6,000 mg.

1 Claim, No Drawings

ANTIBACTERIAL SUBSTITUTED AZETIDINONES

The present invention relates to anti-bacterially active compounds, to their preparation and to compositions containing them.

Belgian Pat. No: 827926 discloses inter alia the compound of the formula (I):

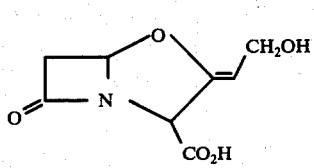
(I)

and its salts and esters. These compounds were shown to be antibacterially active. We have now discovered that it is possible to reduce the double bond in the compound of formula (I) and surprisingly still retain antibacterial activity.

Accordingly the present invention provides compounds of the formula (II):

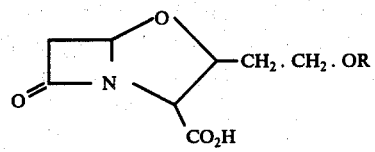
(II)

and salts and esters thereof wherein R is a hydrogen atom or an acyl group.

The stereochemistry at the 3 and 7 positions of the compound of the formula (II) is the same as found in naturally occurring penicillins and cephalosporins.

The hydrogenation reaction generally produces a mixture of two optical isomers. The present invention extends to each of these isomers as well as to mixtures of these isomers.

The group R in formula (II) may represent a hydrogen atom or a wide variety of acyl groups which may contain up to 16 carbon atoms. However, in general, when R is an acyl group it more suitably contains not more than 12 carbon atoms. Generally R is an acyl group as in the acylamino side chain of a known antibacterially active penicillin or cephalosporin.

Particular acyl groups which may be considered worthy of mention include those of the formula $CO.R_1$ where $R_1$ is a methyl, ethyl, propyl, butyl, pentyl, hexyl, benzyl, phenyl, cyanomethyl, phenoxymethyl, α-phenoxyethyl, 4-pyridylmethyl, 4-pyridylthiomethyl, 2-thienylmethyl, 3-thienylmethyl, α-hydroxybenzyl, α-aminobenzyl, α-amino-p-hydroxybenzyl, α-ureidobenzyl, sydnonylmethyl, tetrazolylmethyl, α-carboxybenzyl, α-methoxycarbonylbenzyl, α-phenoxycarbonylbenzyl, α-indanylcarboxybenzyl, α-benzyloxycarbonylbenzyl, and the like groups.

Suitably $R^1$ is group of the sub-formula (a):

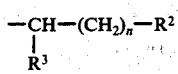
(a)

wherein $n$ is 0 or an integer from 1 to 3; $R^2$ is an hydrogen atom or a phenyl or phenoxy group and $R^3$ is an hydrogen atom or a $C_{1-3}$ alkyl, $C_{1-3}$ alkoxy or $CC_2R^4$ group where $R^4$ is an hydrocarbon group of 1 to 8 carbon atoms.

Suitably $n$ is 0 or an integer from 1 to 3; $R^2$ is an hydrogen atom or a phenyl or phenoxy group and $R^3$ is an hydrogen atom or $CO_2R^4$ group wherein $R^4$ is a phenyl, benzyl or benzhydryl group.

Preferred acyl groups include those of the sub-formula —CO—$R^5$ wherein $R^5$ is a methyl group or a methyl group substituted by a $C_{1-3}$ alkyl group, a phenyl or phenoxy group or by a phenyl group and an ester group $CO_2R^6$ wherein $R^6$ is a phenyl or benzyl group.

Most suitably R is an hydrogen atom so that particularly suitable compounds of this invention include those of the formula (III):

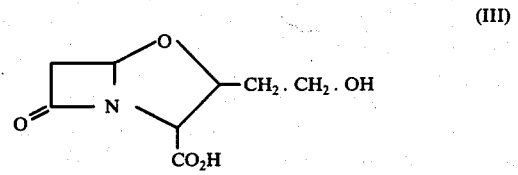
(III)

and salts and esters thereof.

Most suitably salts of the compounds of the formula (II) and (III) are pharmaceutically acceptable salts such as the sodium, potassium, calcium, magnesium, aluminium, ammonium and conventional substituted ammonium salts. Preferred salts of the compounds of the formulae (II) and (III) include the sodium and potassium salts.

Most suitably esters of the compounds of the formulae (II) and (III) are those which are readily convertable by chemical means to the compound of formula (II) or (III) per se or a salt thereof or those which are converted in-vivo to the compound of the formula (II) and (III) per se or a salt thereof. In-vivo conversion may be chemical or biochemical, for example by chemical or enzymatic hydrolysis in human blood.

Suitable esters include those of the sub-formulae (a) - (d):

(a)

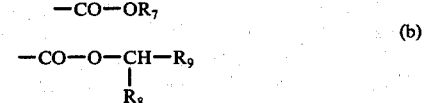
(b)

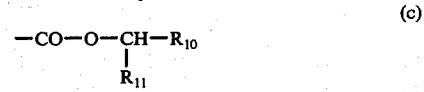
(c)

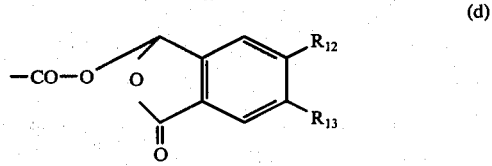
(d)

wherein $R_7$ is an alkyl group of 1–6 carbon atoms; $R_8$ is a hydrogen atom or a methyl group; $R_9$ is an alkyl group of 1–6 carbon atoms or a phenyl group; $R_{10}$ is a hydrogen atom or a phenyl or methoxy phenyl group; $R_{11}$ is a phenyl or methoxy phenyl group; $R_{12}$ is a hydrogen atom or a methyl or methoxy group and $R_{13}$ is a hydrogen atom or a methyl or methoxy group.

In a composition aspect the present invention provides a pharmaceutical composition which comprises a compound of the formula (II) as hereinbefore defined or a salt or ester thereof. Such compositions will also comprise a pharmaceutically acceptable carrier.

Most suitably the compound of the formula (II) present in the compositions of this invention will be a compound of the formula (III) as hereinbefore defined or a pharmaceutically acceptable salt thereof.

The compositions of this invention will normally be adapted for administration to humans and other mammals, for example, in conventional modes of treatment of diseases of the skin or of the urinary tract.

Suitable forms of the compositions of this invention include tablets, capsules, solutions or creams for topical application, syrups, suspensions, reconstitutable powders and sterile forms suitable for injection or infusion. Such compositions may contain conventional pharmaceutically acceptable materials such as diluents, binders, colours, flavours, preservatives, disintegrants, and the like in accordance with conventional pharmaceutical practice.

Normally between 50 and 6000 mg of the compositions of the invention will be administered each day of treatment but more usually between 500 and 3000 mg of the composition of this invention will be administered per day.

The present invention also provides a process for the preparation of a compound of the formula (II) as hereinbefore defined which process comprises the reduction of a compound of the formula (IV):

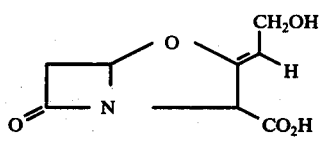

(IV)

or a salt or ester thereof, followed, if desired, by acylation of a free alcoholic hydroxyl group and/or esterification of any free or salted carboxylic group.

This process generally produces a mixture of two epimers which are frequently present in a roughly 2:1 mixture.

The reduction reaction of the present invention is normally a hydrogenation reaction carried out in the presence of a transition metal catalyst. Suitable catalysts include palladium, platinum, platinum oxide, nickel and other conventional catalysts. A particularly suitable catalyst is 10% palladium on charcoal.

Most suitably the weight of catalyst present is not more than the weight of compound of the formula (IV) or salt or ester thereof present. Hydrogenation may proceed using a low, medium or high pressure of hydrogen and at any non-extreme temperature. Most suitably the reaction is carried out at a temperature between −10° C and +100° C, such as −5° C to 40° C, for example −5° to +20° C.

If low pressures of hydrogen are used (for example, about 1 atmosphere) at an approximately ambient temperature then, in general, the hydrogenation takes many hours for completion. Carrying out the reaction at higher pressures and/or higher temperatures can lead to a faster reaction.

The reaction may be carried out in a solvent conventionally used for such reactions, for example, tetrahydrofuran, ethyl acetate or the like.

If the compound of the formula (II) is present as an ester which is readily reduceable to a free or salted carboxylic acid group, then during the prolonged hydrogenation reaction which leads to the reduction of the carbon-carbon double bond, the ester group is converted to a carboxylic acid group or a salt thereof. Thus if it is desired to produce an ester of a compound of the formula (II) which is labile to hydrogenolysis conditions such compounds should be prepared by the esterification of a compound of the formula (II) per se or a salt thereof.

From a further aspect the present invention provides a process for the preparation of compounds of the formula (II) as hereinbefore defined wherein R is an acyl group which process comprises the acylation of the corresponding compound of the formula (III):

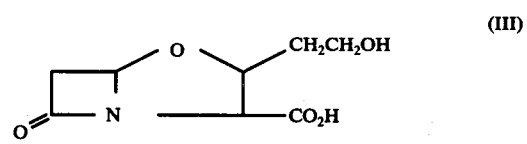

(III)

or an ester thereof.

Suitable acylating agents for this reaction will be similar to those used in the preparation of penicillins or cephalosporins from 6-aminopenicillanic acid or 7-aminocephalosporanic acid. However, the β-lactam ring in compounds of formula (II) are frequently more reactive than those of many penicillins or cephalosporins so that in general particularly mild reaction conditions are preferred.

Generally the acylation reaction of this invention is carried out in an inert organic solvent. Suitable solvents include chloroform, methylene chloride, tetrahydrofuran, dimethylformamide, dimethylsulphoxide, acetone and the like.

Generally the acylation reaction of this invention is carried out at a non-extreme temperature, for example, at ambient or slightly depressed temperatures, such as in the range −10° C to +20° C, more suitably −5° C to 10° C, for example, at about 0° C to 5° C.

An acid acceptor may be present if desired, for example, potassium carbonate if the solvent is acetone.

A convenient method of acylating compounds of the formula (III) comprises the reaction of the compound of formula (III) with an acid ROH in the presence of a condensation promoting agent such as a carbodiimide, carbodiimidazole or the like agent. This reaction is best performed on esters of the compounds of the formula (III) so that if a salt of the compound of the formula (II) is required the reaction is generally performed on a benzyl ester which is later subjected to hydrogenolysis.

A particularly suitable condensation promoting agent is dicyclohexycarbodiimide.

If the acyl group R contains a reactive substituent which would be affected by or interfere with the acylation reaction then that group may be reversibly protected in conventional manner.

The following Examples illustrate the invention:

EXAMPLE 1

Methyl 3-(2'-hydroxyethyl) - 7 oxo - 1 - aza - 4 - oxabicyclo [3,2,0] - heptane - 2 - carboxylate

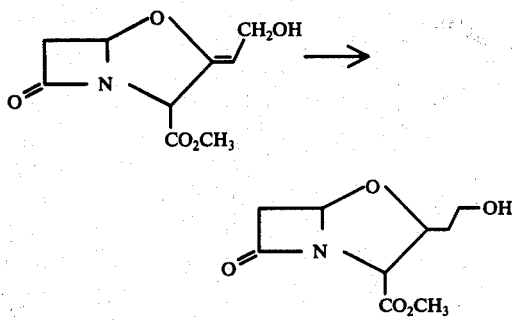

Methyl 3-)2'-hydroxyethilidine) - 7 - oxo - 1 - aza - 4 oxabicyclo [3,2,0] heptane - 2 - carboxylate (e1) (80 mg) in ethyl acetate (5 ml) was hydrogenated over 10% Pd/C (25 mg) for 24 hours at ambient temperature and pressure. A further quantity of catalyst (25 mg) was added and the hydrogenation continued for 24 hours. Evaporation of the solvent and chromatography of the resulting oil on silica gel yielded as the major product the title compound (e2) (24.6 mg; 30%) as a 2:1 mixture of epimers) max. (CHCl$_3$): 3400 (OH), 1790, 1740 cm$^{-1}$; n.m.r. (CDCl$_3$): 1.7 - 2.4 (2H, br. m, CH—CH$_2$ signal from two isomers), 2.20 (1H, br. s, OH, exchangeable with D$_2$O), 2.95 (1H, d, J = 17Hz, 6β—CH), 3.47 and 3.50 (1H, two double doublets, J = 17Hz and J' = 2.5Hz, 6α-CH from both isomers), 3.88 (3H, s, CO$_2$CH$_3$), 4.2 to 4.9 (4H, complex pattern, OCH$_2$, 2-CH and 3-CH from both isomers), 5.43 (2/3H, d, J = 2.5Hz, 5-CH [major isomer]), 5.66⅓ (1/3H, br. d, J = 2.5Hz, 5-CH [minor isomer]).

EXAMPLE 2

Methyl 3(2'-acetoxyethyl)-7-oxo-1-aza-4-oxabicyclo [3,2,0]heptane -2-carboxylate

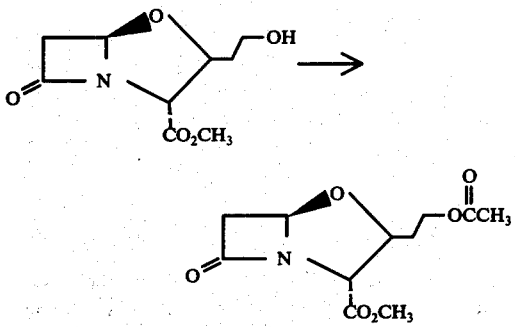

The dihydroclavulanate (e2) (130 mg) in dry acetone (5 ml) containing pyridine (52 mg) was cooled to 0°. Glacial acetic acid (40 mg) was added, followed by D.C.C.I. (138 mg) and the mixture stirred at room temperature overnight. The solution was cooled to 0° and a further quantity of glacial acetic acid (100 mg) was added. The reaction was stirred at room temperature for a further 48 hours, the solution filtered and the solvent evaporated to yield an oil which provided, after chromatography, the title compound (e3) (76 mg; 50%) as the major product (2:1 mixture of epimers); ν max. (CHCl$_3$): 1790, 1740 cm$^{-1}$, n.m.r. (CDCl$_3$): 1.7 - 2.4 (2H, br. m, CHCH$_2$ signal from two isomers), 2.12 (3H, s, CCH$_3$), 2.93 (1H, d, J = 17Hz, 6β-CH), 3.47 and 3.50 (1H, two double doublets, J = 17Hz and J' = 2.5Hz, 6α-CH from both isomers), 3.87 (3H, s, CO$_2$CH$_3$), 4.2 to 4.9 (4H, complex pattern, OCH$_2$, 2-CH and 3-CH from both isomers), 5.43 (⅔H, d. J = 2.5Hz, 5-CH [major isomer]), 5.66δ (⅓H, br. d, J = 2.5Hz, 5-CH (minor isomer); m.w. (mass spectrometry) 257; [α]$_D^{22}$ = + 96.2. (MeOH). Further chromatography afforded separation of the two epimers, the least polar isomer being the minor epimer; ν max. (CHCl$_3$): 1790, 1740 cm$^{-1}$, n.m.r. (CDCl$_3$): 1.89 (2H, br. t, J = 6Hz, CH—CH$_2$), 2.05 (3H, s,

OCCH$_3$), 2.88 (1H, dd, J = 17Hz, J' = 1Hz, 6β-CH), 3.41 (1H, dd, J = 17Hz, J' = 2.5Hz, 6α-CH), 3.78 (3H, s, CO$_2$CH$_3$), 4.25 (2H, br. t, J = 6Hz, OCH$_2$); irradiation of the triplet at 1.89δ leads to collapse of the triplet at 4.25δ to a singlet), 4.55 and 4.72 (2H, m and d respectively, irradiation at 1.89δ causes collapse of the multiplet and two doublets observed at 4.55 and 4.72 may be assigned to the 3-CH and 2-CH), 5.56δ (1H, dd, J = 2.5Hz, J' = 1Hz, 5-CH); [α]$_D^{20}$ = + 78.5 (MeOH).

The more polar isomer corresponded to the major epimer (CHCl$_3$) 1790, 1740cm$^{-1}$; n.m.r. (CDCL$_3$): 2.05 (3H, s,

OCCH$_3$), 2.16 (2H, br. t, J = 6Hz CH—Cl$_2$); 2.86 (1H, d, J = 17Hz, 6β-CH), 3.37 (1H, dd, J = 17Hz, J' = 2.5Hz, 6α-CH), 3.77 (3H, s, CO$_2$CH$_3$) 4.21 (2H, br. t, J = 6Hz, OCH$_2$, irradiation of the triplet at 2.16 leads to collapse of the triplet at 4.21δ to a singlet). 4.21 and 4.48 (2H, i m, irradiation at 2.16δ causes collapse of the multiplet and two doublets absorbing at 4.21 and 4.48δ may be assigned to the 3-CH and 2-CH, 5.32δ (1H, d, J = 2.5Hz, 5-CH); [α]$_D^{20}$ = + 93.3 (MeOH).

EXAMPLE 3

Methyl 3[2'-(monobenzyl phenylmalonyl) ethyl]-7-oxo-1-aza-4-oxabicyclo[3,2,0]heptane-2-carboxylate

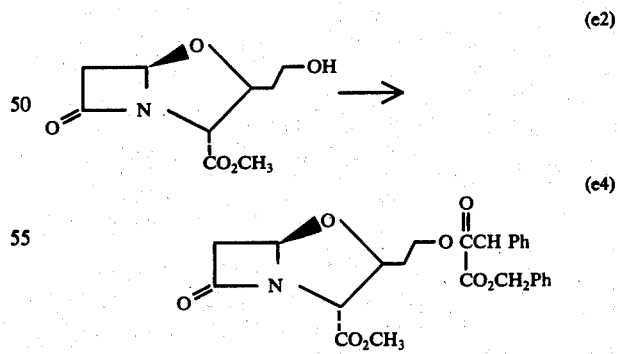

The dihydroclavulanate (e2) (23.3 mg) as a 5:1 mixture of epimers in methylene chloride (3 ml) was cooled to 0° and treated with monobenzyl-phenylmalonate (27 mg) followed by D.C.C.I (20.6 mg). The solution was stirred at room temperature overnight, filtered, washed with water (ml), dried over MgSO$_4$ and evaporated to yield an oil which after chromatography furnished the title compound (e4) as essentially one epimer in the major fraction (28 mg; 60%), ν max. (CHCl₃): 1790, 1750, 1740 cm⁻¹; n.m.r. (CDCl₃): 2.05 (2H, br. m, CH—CH₂), 2.80 (1H, d, J = 17Hz, 6β-CH), 3.30 (1H, dd, J = 17Hz, J' = 2.5Hz, 6α-CH), 3.71 (3H, s, CO₂CH₃) 4.00 - 4.60 (2H, br. m, 3-CH and 2-CH), 4.28 (2H, t, J = 6Hz, OCH₂), 4.68 (1H, s, CH-Ph), 5.18 (2H, s, CO₂CH₂Ph), 5.20 (1H, m, 5-CH, signal partially obscured by benzylic CH₂), 7.35δ (10H, s, aromatic protons); [α]$_D^{22}$ = +59° (MeOH).

EXAMPLE 4

Benzyl 3-(2' - hydroxyethyl) - 7 - oxo - 1 - aza - 4 - oxabicyclo [3,2,0] heptane - 2 - carboxylate

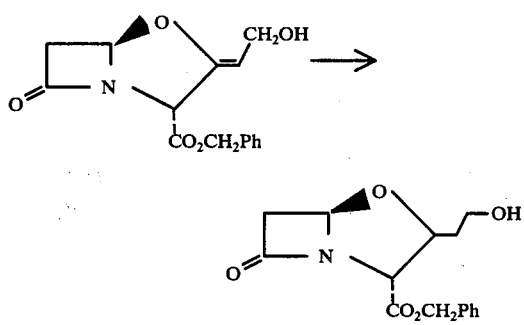

Benzyl 3-(2' - hydroxyethylidene) - 7 - oxo - 1 - aza - 4 - oxabicyclo [3,2,0] heptane ): 2 -carboxylate (e5) (650 mg) in ethyl acetate (20 ml) was hydrogenated over platinum oxide (650 mg) for 2 hours. The solution was filtered through celite and treated with a solution of diazotoluene in ether at 0°. Evaporation of the solvent and chromatography yielded as the major product the title compound (e6) (82 mg; 13%) as a 1:1 mixture of epimers. Further chromatography afforded separation of the least polar epimer, ν max. (CHCl₃2.92 (13400 (OH) 1790, 1740 cm⁻¹, n.m.r. (CDCl₃): 1.70 (1H, br. s, OH exchangeable with D₂O) 2.09 (2H, br. t, J = 6Hz, CH₂OH) 2.92 (1H, d, J = 17Hz, 6β-CH) 3.42 (1H, dd, J = 2.5Hz and J' = 17Hz, 6α-CH), 3.78 (2H, br. t, J = 6Hz, CH—CH₂) 4.20 to 4.80 (2H, br. m, 3-CH and 2-CH), 5.28 (2H, s, CH₂Ph), 5.39 (1H, d, J = 2.5Hz, 5-CH), 7.49δ (5H, s, aromatic protons). The remaining fractions contained a mixture of epimers, ν max. (CHCl₃): 3400 (OH) 1790, 1740 cm⁻¹; n.m.r. (CDCl₃): 1.70 (1H, brs, OH exchangeable with D₂0), 1.74 and 2.09 (2H, two broad triplets, J = 6Hz, CH₂OH for both epimers), 2.92 (1H, br. d, J = 17Hz, 6β-CH from both epimers), 3.40 and 3.35 (1H, two double doublets, J = 2.5Hz and J' = 17Hz, 6α-CH), 3.75 (2H, two broad triplets, J = 6Hz, CH—CH₂), 4.2 to 4.9 (2H, br. m, 3-CH and 2-CH), 5.28 (2H, s, PhCH₂-), 5.39 (½H, d, J = 2.5Hz, 5-CH from the least polar epimer), 5.62δ (½H, dd, J = 2.5Hz, J' = 1Hz, 5-CH from the more polar epimer). [α]$_D^{22}$ = +67.6° (MeOH), m.w. (mass spectrometry) 291.

EXAMPLE 5

Sodium 3-(2'-hydroxyethyl)-7-oxo-1-aza-4-oxabicyclo[3,2,0] heptane-2-carboxylate

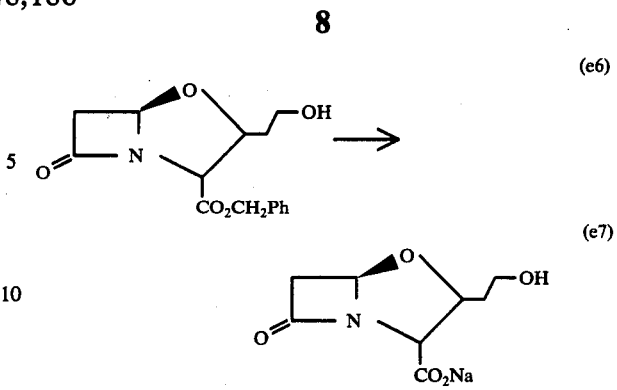

The dihydroclavulanate (e6) (24 mg) in 10% aqueous ethanol (2 ml) containing one equivalent of NaHCO₃ (7 mg) was hydrogenated over 10% Pd/C (20 mg) for half an hour. The solution was filtered and the solvent evaporated to yield the title compound (e7) (16 mg; 83%) as an amorphous solid, ν max. (KBr): 3400 (OH), 1770 cm⁻¹, n.m.r. (D₂O): 1.5 to 2.20 (2H, br. m, CH₂OH for both epimers), 2.85 (1H, d, J = 17Hz, 6β-CH), 3.38 (1H, dd, J = 17Hz, J' = 2.5Hz, 6α-CH), 3.70 (2H, t, J = 6Hz, CH—CH₂), 3.90 to 4.50 (2H, m, 3-CH and 2-CH), 5.35 (⅔H, d J = 2.5Hz, 5-CH from the first epimer), 5.40δ (⅓H, br. d, J = 2.5Hz, 5-CH from the second epimer. [α]$_D^{21}$ = +53° (50% aq. MeOH).

EXAMPLE 6

Benzyl 3-[2'-phenoxyacetoxyethyl]-4-oxabicyclo[3,2,0] heptane-2-carboxylate

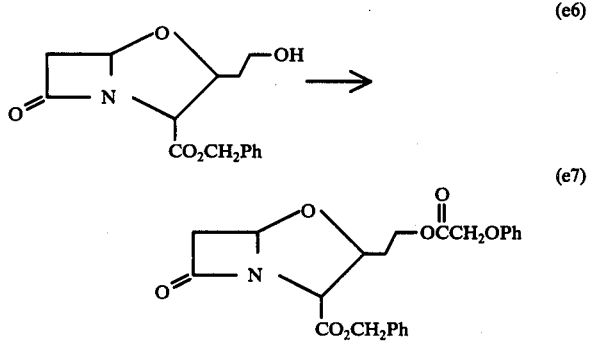

Phenoxyacetic acid (38 mg) and the dihydroclavulanate (e6) (72 mg) in methylene chloride (5 ml) were treated with D.C.C.I. (52 mg) at 0°. The mixture was stirred at room temperature overnight. The solution was cooled at 0° and a further two equivalents of phenoxyacetic acid (80 mg) followed by two equivalents of pyridine (40 mg) and one equivalent of D.C.C.I. (52 mg) were added. The reaction was allowed to warm to room temperature and stirred for three hours. The solution was filtered and chromatographed to provide the title compound (e8) (99 mg; 93%) as a mixture of epimers. The product was further purified by h.p.l.c. The least polar isomer was collected as a colourless oil ν max. (CHCl₃): 1790, 1745 cm⁻¹; n.m.r. (CDCl₃): 1.80 (2H, t, J = 6Hz, CH—CH₂), 2.86 (1H, d, J = 17Hz, 6β-CH), 3.42 (1H, dd, J = 17Hz, J' = 2.5Hz, 6α-CH), 4.34 (2H, br. t, J = 6Hz, CH₂—0), 4.2 to 4.8 (2H, m, 3-CH and 2-CH), 4.70 (2H, s, PhOCH₂—), 5.28 (2H, s, PhCH₂), 5.57 (1H, br. d, 5-CH), 6.8 to 7.5 (5H, m, PhO), 7.50δ (5H, s, PhCH₂); [α]$_D^{23}$ = +93° (MeOH). The more polar epimer was collected as a colourless oil containing approximately 20% of the first epimer, ν max. (CHCl₃): 1790, 1745 cm⁻¹; n.m.r. (CDCl₃; second epimer): 2.17 (2H, t, J = 6Hz, CH CH₂), 2.87 (1H, d. J = 17Hz, 6β-CH), 3.38 (1H, dd, J = 17Hz, J' = 2.5Hz), 4.35 (2H, t, J = 6Hz, CH₂—O) 4.2 – 4.8 (2H, m, 3-CH and 2-CH, 4.63 (2H, s, PhOCH₂), 5.26 (2H, s, PhCH₂), 5.32 (1H, d, J = 2.5Hz, 5-CH), 6.8 to 7.5 (5H, m, PhO), 7.50δ (5H, s, PhCH₂). $[\alpha]_D^{23} = +73°$(MeOH).

EXAMPLE 7

Sodium 3-[2'-(phenoxyacetoxy)ethyl]-7-oxo-1-aza-4-oxabicyclo [3,2,0]heptane-2-carboxylate

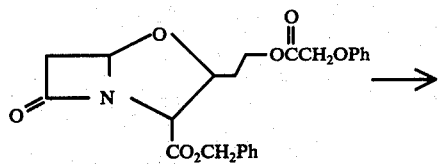

(e8)

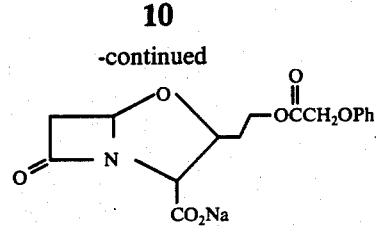

(e9)

The dihydroclavulanate (e8) (21 mg; 4:1 mixture of epimers) was dissolved in 10% aq. EtOH (2 ml) containing ethyl acetate (1 ml) and one equivalent of NaHCO₃ (4.2 mg). The solution was hydrogenated over 10% pd/C (20 mg) for fifteen minutes. The solution was filtered through celite and the solvent evaporated to yield the title compound (e9) (12mg; 64%) as a white amorphous solid after trituration with ethanol and then ether. ν max. (KBr): 3400 (OH), 1760 cm⁻¹ (broad); n.m.r. (D₂O): 2.15 and 1.90 (2H, two multiplets CH—CH₂ for the major and minor isomers respectively), 2.83 (1H, d, J = 17Hz, 6β-CH), 3.41 (1H, dd, J = 17Hz, J' = 2.5Hz, 6α-CH), 4.38 (2H, t, J' = 6Hz, CH₂O), 4.10 to 4.80 (2H, m, 2-CH and 3-CH), 4.80 (2H, s, PhOCH₂), 5.30 and 5.47 (1H, two multiplets, 5-CH for the major and minor epimers respectively), 6.8 to 7.6δ (5H, m, PhOCH₂). $[\alpha]_D^{127} = +60.6°$ (50% aq. MeOH).

We claim:
1. The compound which is sodium 3-[2' -(phenoxyacetoxy)ethyl]-7-oxo-1-aza-4-oxabicyclo[3,2,0]heptane-2-carboxylate.

* * * * *